United States Patent
Manek et al.

(10) Patent No.: US 9,505,988 B2
(45) Date of Patent: Nov. 29, 2016

(54) CIRCULATION AID FOR PRIMARY FRACTIONAL QUENCH LOOPS

(75) Inventors: Maria Beata Manek, Meadows Place, TX (US); Meha H. Shah, Houston, TX (US); Daniel K. Frye, League City, TX (US)

(73) Assignee: NALCO Company, Naperville, IL (US)

( * ) Notice: Subject to any disclaimer, the term of this patent is extended or adjusted under 35 U.S.C. 154(b) by 1010 days.

(21) Appl. No.: 13/276,599

(22) Filed: Oct. 19, 2011

(65) Prior Publication Data

US 2013/0098466 A1    Apr. 25, 2013

(51) Int. Cl.
| | | |
|---|---|---|
| F15D 1/00 | (2006.01) | |
| C10G 29/24 | (2006.01) | |
| C10G 29/22 | (2006.01) | |
| C07C 7/20 | (2006.01) | |
| C10G 29/20 | (2006.01) | |
| C10G 9/00 | (2006.01) | |

(52) U.S. Cl.
CPC ............... *C10G 29/24* (2013.01); *C07C 7/20* (2013.01); *C10G 9/00* (2013.01); *C10G 29/20* (2013.01); *C10G 29/22* (2013.01); *C10G 2300/302* (2013.01); *Y02P 20/51* (2015.11); *Y10T 137/0391* (2015.04)

(58) Field of Classification Search
CPC .............. F15D 1/00; F17D 1/16; F17D 1/17; F17D 1/18; C10G 9/12; B01J 13/00
USPC .................... 137/13; 585/3, 4, 435
See application file for complete search history.

(56) References Cited

U.S. PATENT DOCUMENTS

| | | | |
|---|---|---|---|
| 5,073,248 A | 12/1991 | Stephenson et al. | |
| 5,494,607 A | 2/1996 | Manek et al. | |
| 5,824,829 A * | 10/1998 | Maeda et al. | 585/3 |
| 5,985,940 A * | 11/1999 | Manek et al. | 516/31 |
| 7,678,745 B2 | 3/2010 | Parris et al. | |
| 2009/0312210 A1 * | 12/2009 | Grisso et al. | 508/379 |
| 2010/0062957 A1 | 3/2010 | Bertram et al. | |

FOREIGN PATENT DOCUMENTS

| | | |
|---|---|---|
| CN | 1566042 A | 1/2005 |
| CN | 101062880 A | 10/2007 |
| CN | 101838522 A | 9/2010 |
| JP | H 06287587 A | 10/1994 |
| JP | 2010-065226 A | 3/2010 |

OTHER PUBLICATIONS

Huang Zhiyu, et al., "Study on Acrylate-Styrene-Maleic Anhydride Ternary Polymer Oil-soluble Viscosity-Reducing Agent", Journal of Jilin Institute of Chemical Technology, vol. 20, No. 4, Dec. 2003.

* cited by examiner

*Primary Examiner* — Sharon Pregler
(74) *Attorney, Agent, or Firm* — Eric D. Babych; Brinks Gilson & Lione

(57) ABSTRACT

The invention directed to a method of reducing the increase in viscosity and the drop in the heat transfer coefficient that commonly occurs with quenching media which is repeatedly circulated through a hot reaction vessel. The method comprises adding a preserving composition to the quenching media. The composition comprises: a) high temperature polymerization inhibitor, b) a tar dispersant, and c) a viscosity reducer. The method allows the quenching media to remain effective longer than would otherwise be the case. By doing so this prevents having to devote excessive resources for such problems as: controlling heat recovery, viscosity increases, product downgrades or having to operate equipment at temperatures beyond their optimum performance designs.

20 Claims, No Drawings

CIRCULATION AID FOR PRIMARY FRACTIONAL QUENCH LOOPS

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to methods and compositions for reducing the viscosity of circulating media used in primary fractionators of ethylene plants. In an ethylene plant, hot cracked gases from furnaces need to be cooled down (quenched) for further processing and fractionation. This cooling process takes place in the quench system, which in the case of liquid and mixed feed crackers, consists of a series of transfer line exchangers (TLX or TLE), primary fractionator or quench oil tower, quench oil loop, and auxiliary equipment, (i.e. filters, optional fuel oil stripper, etc.). After initial cooling (quenching) in the TLX, cracked products are fed to the distillation tower (primary fractionator or quench oil tower), which separates light products to the top (pyrolysis gasoline) and heavier hydrocarbons to the bottoms. A portion of the bottom product is circulated via the quench oil loop hack to the TLX as the quenching medium. The immense heat recovered through the quench oil system is used to produce dilution steam, which in turn is returned to the cracking furnaces aiding in overall heat recovery.

High temperatures and long residence times in the circulation (quench oil) loop are conductive to the heavy molecules produced in the cracking furnaces to agglomerate into large polynuclear aromatic species, often referred to as tars. Tars increase the viscosity of the circulating media thus increasing the potential for fouling in the tower and in turn negatively affecting heat recovery and proper fractionation.

As the quenching material's viscosity increases, its heat transfer coefficient drops. Over time this can result in severely reduced heat recovery, less steam production in dilution steam systems, and significant costs of import steam required for cracking. Additionally, as the media becomes harder to pump, it works less effectively, or needs to be supplemented with imported flux oil. In some cases the quenching media becomes so ineffectual that at least some portions of the plants must be operated at temperatures beyond their design limitations. All this results in significant costs and problems with maintenance and product quality.

Prior art methods of mitigating viscosity increases in quench media involve adding specially formulated antifoulants that prevent heavy tars from aggregating and depositing, thereby improving the tar's flow characteristics. U.S. Pat. No. 5,985,940 describes the use of phenol-formaldehyde resins to control viscosity in quenching media. The prior art methods, however, lose effectiveness when significant amounts of residual reactive monomers are present in the effluent of the cracking process. Recent changes in industry practice involve using different feedstocks which result in large amounts of residual reactive monomers which impair the effectiveness of these antifoulants. This is causing unpredictable changes in the mechanisms and characteristics of the quenching media and is once again resulting in significant problems in cost, product quality and maintenance. Thus there is clear need and utility for methods and compositions useful in reducing the impact of tar on the circulating media in primary fractionator quench loops.

The art described in this section is not intended to constitute an admission that any patent, publication or other information referred to herein is "Prior Art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

At least one embodiment of the invention is directed to a method of reducing an increase in viscosity or maintaining viscosity and a drop in the heat transfer coefficient of quenching media which is repeatedly circulated through a hot circulation system. The method comprises the step of adding a preserving composition to the quenching media. The composition comprises: a) high temperature polymerization inhibitor, b) a tar dispersant, and c) a viscosity reducer.

The composition may further comprise a high boiling point solvent. The high temperature polymerization inhibitor may be 1-naphthol, or hindered phenol, or a combination thereof. The tar dispersant may be alkyl substituted phenol formaldehyde resin. The viscosity reducer may be alpha olefin-alkyl maleate co-polymer. The composition may be added, to the quenching media to result in an amount of 100-10000 ppm. The quenching media may be quench oil. The hot circulation loop may be a primary fractionator quench oil loop in an ethylene plant. The hot circulation loop may be one selected from the list consisting of a primary fractionator in ethylene plant or an EDC/VCM application. The residence time of the quenching media in the reaction vessel may be highly variable. The temperature of the quenching media in the reaction vessel may be between 20 and 300° C.

Additional features and advantages are described herein, and will be apparent from, the following Detailed Description.

DETAILED DESCRIPTION OF THE INVENTION

The following definitions are provided to determine how terms used in this application, and in particular how the claims, are to be construed. The organization of the definitions is for convenience only and is not intended to limit any of the definitions to any particular category.

"High Temperature Polymerization Inhibitor" means a composition of matter that inhibits the formation of polymers from monomer units present in temperatures in excess of 150° C., which includes but is not limited to hindered phenols, 1-naphthoic aryl substituted aromatic diamines, alkyl substituted aromatic diamines, and combinations thereof.

"Tar Dispersant" means a composition of matter comprising a molecule having a hydrocarbon group, a polar group (for example a nitrogen or oxygen functional group), and a connecting group connected to both the hydrocarbon group and the polar group, the composition capable of effectively inhibiting the agglomeration or breaking up agglomerates of tars in a liquid, and dispersing them throughout the liquid, which includes but is not limited to alkyl substituted phenol-formaldehyde resins, alkyl substituted phenol-polyethylene-polyamine-formaldehyde resins, polyacrylate copolymers, and combinations thereof.

"Viscosity Reducer" means a composition of matter that reduces viscosity of hydrocarbon mixtures at elevated temperatures above 150° C. which includes but is not limited to α-olefin maleic acid copolymers.

In the event that the above definitions or a description stated elsewhere in this application is inconsistent with a meaning (explicit or implicit) which Is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology*, 5th Edition, (2005), (Published by Wiley, John & Sons, Inc.) this definition shall control how the term is to be defined in the claims.

In at least one embodiment the performance properties of a quenching medium which is repeatedly circulated into cracked material to cool the material is preserved by adding a novel composition of matter. The composition comprises a high temperature polymerization inhibitor, a tar dispersant, and a viscosity reducer. In at least one embodiment the composition further comprises a high boiling point solvent. This composition prevents tars from agglomerating, inhibits polymerization of residual monomers from the cracking process (such as styrene, indene, monounsaturated hydrocarbons, polyunsaturated hydrocarbons, and any combination thereof) and prevents these materials from interacting, thus effectively reducing viscosity of the quenching material. The prevention persists even when the quenching media is re-circulated many times over a long period of time. Moreover, the prevention resulting from the composition is an unexpected effect that results from a synergism caused by the combination of these three components. This causes the observed degree of prevention to exceed the sum of each of rise individual prevention effects of each of the three components.

In at least one embodiment the tar dispersant is one selected from the list consisting of alkyl substituted phenol formaldehyde resins, polyacrylate copolymer, alkyl substituted phenol-polyethylene-polyamine-formaldehyde resins, and any combination thereof. In at least one embodiment representative tar dispersants are those described in U.S. Pat. No. 5,985,940.

In at least one embodiment the polymerization inhibitor is 1-naphthol or a hindered phenol.

In at least one embodiment the polymerization inhibitor is an amine antioxidant. While a composition comprising an amine antioxidant and a phenol formaldehyde resin is described in Chinese Patent Application CN 101062880, it does not disclose adding a viscosity reducer. Moreover this reference makes no teaching or suggestion that the combination of the three would result in a preservation effect in excess of the sum of each of the individual prevention effects of each of the three components.

In at least one embodiment the composition is effective for a cracked material in which reactive monomers exceeds 1% of the cracked material. In at least one embodiment the composition is effective for a cracked material in which reactive monomers are between 1-10% of the cracked material.

Without being limited in the scope of the claims it is believed that the composition is effective because it allows the inhibition effect to be present throughout the entire system being quenched and not only in one portion of it. In prior art uses of polymerization, the physical properties of the inhibitors limit them to the top portion of a fractionator and therefore they do not function effectively in the bottoms of the fractionator. In the instant invention the composition of matter allows the inhibitor to manifest at the bottoms as well and as a result causes a much greater preservative effect.

In at least one embodiment the composition comprises 1-10% (preferably 5%) tar dispersant, 1-10% (preferably 5%) hindered phenol, 1-naphthol, or a combination of hindered phenol and 1-naphthol, 8-30% (preferably 20%) viscosity reducer, and 50-90% (preferably 70%) of heavy aromatic naphtha. In at least one embodiment the naphtha functions as the solvent.

In at least one embodiment the composition is added in a dosage of 100 to 10,000 ppb in the quenching medium. In will be recognized that the ideal dosage of composition may vary based on the viscosity of the medium and more viscous media require greater dosages of composition. In at least one embodiment the composition is directly injected into the circulation loop. In at least one embodiment the residence time is 1 hour to 10 days (preferably 2-5 days).

In at least one embodiment the composition prevents viscosity increases and heat transfer coefficient drops in quenching media in industrial facilities including but not limited to quench oil loops of primary fractionators in ethylene plants, EDC/VCM applications, and any combination thereof.

EXAMPLES

The foregoing may be better understood by reference to the following examples, which are presented for purposes of illustration and are not intended to limit the scope of the invention.

A portion of quench oil from a circulation loop of primary fractionator in an ethylene plant was obtained. Laboratory analysis of the portion showed that it contained 1-2% reactive monomers. The portion was then divided into a number of samples to which various amounts of native pyrolysis gasoline was added to simulate conditions of the quench oil loop. This resulted in samples having as much as 1-10% reactive monomers. The samples then had various amounts of one, two, or all three components of the inventive composition added to them.

Viscosity profiles were taken of the refluxed samples after specific periods of time (4 to 20 hours) and were measured over a range of temperatures 40-150° C. using a Brookfield rheometer with Thermosel® attachment. The percent reductions in viscosity are reported on Tables 1 and 2 for the low and high endpoints of the measurements taken.

TABLE I

Percent Viscosity Reduction at 40° C.
(quench oil with 1% pyrolysis gasoline)

| Sample# | Additive at 600 ppm | % Reduction after 4 hours reflux | % Reduction after 20 hours reflux |
|---------|---------------------|----------------------------------|-----------------------------------|
| 1 | Phenol-Formaldehyde resin | 14.31 | 23.65 |
| 2 | Alpha olefin-alkyl maleate copolymer | 13.00 | 43.73 |

TABLE I-continued

Percent Viscosity Reduction at 40° C.
(quench oil with 1% pyrolysis gasoline)

| Sample# | Additive at 600 ppm | % Reduction after 4 hours reflux | % Reduction after 20 hours reflux |
|---|---|---|---|
| 3 | 1-naphthol | 20.44 | 46.20 |
| 4 | Combination of 2 and 3 (1:1) | 24.45 | 49.85 |
| 5 | Combination of 1, 2, and 3 (1:1:1) | 28.64 | 54.34 |
| 6 | Combination of 1, 2 and 3 (1:4:1) | 27.55 | 52.33 |

TABLE II

Percent Viscosity Reduction at 150° C.
(quench oil with 1% pyrolysis gasoline)

| Sample# | Additive at 600 ppm | % Reduction after 4 hours reflux | % Reduction after 20 hours reflux |
|---|---|---|---|
| 1 | Phenol-Formaldehyde resin | 0 | 7.89 |
| 2 | Alpha olefin-alkyl maleate copolymer | 10.37 | 17.14 |
| 3 | 1-naphthol | 0 | 15.63 |
| 4 | Combination of 2 and 3 (1:1) | 10.37 | 26.95 |
| 5 | Combination of 1, 2, and 3 (1:1:1) | 14.3 | 36.75 |
| 6 | Combination of 1, 2, and 3 (1:4:1) | 13.8 | 30.02 |

The data demonstrates that while each of the three components individually do reduce viscosity somewhat, the presence of all three shows a marked improvement greater than what would be expected by merely summing their individual effectiveness.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Additionally, the invention also encompasses any possible combination of some or all of the various embodiments described and incorporated herein. Furthermore the invention also encompasses combinations in which one, some, or all but one of the various embodiments described and/or incorporated herein are excluded.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of utilizing quenching media, the method comprising the steps of:
   repeatedly circulating a quenching media through a hot circulation system, the quenching media comprising an amount of reactive monomers exceeding about one percent (by weight) of a cracked material as it passes through the hot circulation system, and
   adding a composition to the quenching media, the composition comprising:
   a) high temperature polymerization inhibitor having a first amount,
   b) a tar dispersant, and
   c) a viscosity reducer having a second amount,
   wherein the first amount is about equal to or less than the second amount, the first amount and the second amount determined by weight percentages, and
   wherein the composition reduces viscosity in the quenching media more than a phenol-formaldehyde resin alone.

2. The method of claim 1, wherein the composition further comprises a high boiling point solvent having a boiling point above 150° C.

3. The method of claim 1, wherein the high temperature polymerization inhibitor is 1-naphthol or hindered phenol.

4. The method of claim 1, wherein the tar dispersant is alkyl substituted phenol formaldehyde resin.

5. The method of claim 1, wherein the viscosity reducer is alpha olefin-alkyl maleate co-polymer.

6. The method of claim 1, wherein the composition is added to the quenching media to result in an amount of 100-10000 ppm.

7. The method of claim 1, wherein the quenching media is quench oil.

8. The method of claim 1, wherein the hot circulation loop is a primary fractionator quench oil loop in an ethylene plant.

9. The method of claim 1, wherein the hot circulation loop is one selected from the list consisting of a primary fractionator in ethylene plant or an EDC/VCM application.

10. The method of claim 1, wherein the residence time of the quenching media in the reaction vessel varies between 1 hour and 10 days.

11. The method of claim 1, wherein the temperature of the quenching media in the reaction vessel is between 20 and 300° C.

12. The method of claim 1, wherein a ratio (by weight) of the high temperature polymerization inhibitor to viscosity reducer is 1:1.

13. The method of claim 1, wherein a ratio (by weight) of the high temperature polymerization inhibitor to viscosity reducer is 1:4.

14. The method of claim 1, wherein the tar dispersant is free of phenol-formaldehyde resin.

15. The method of claim 1, wherein the tar dispersant is a polyacrylate copolymer.

16. A method of utilizing quenching media, the method comprising the steps of:

repeatedly circulating a quenching media through a hot circulation system, the quenching media comprising an amount of reactive monomers exceeding about one percent (by weight) of a cracked material as it passes through the hot circulation system, and adding a composition to the quenching media, the composition comprising:

a) high temperature polymerization inhibitor b) a tar dispersant being free of a phenol-formaldehyde resin, and c) a viscosity reducer wherein the polymerization inhibitor has a first amount and the viscosity reducer has a second amount such that the first amount is about equal to or less than the second amount, the first amount and the second amount determined by weight percentages, wherein the composition reduces viscosity in the quenching media more than a phenol-formaldehyde resin alone.

17. The method of claim 16, wherein the tar dispersant is polyacrylate copolymer.

18. The method of claim 16, wherein the ratio of the high temperature polymerization inhibitor to the viscosity reducer is about 1:1.

19. The method of claim 16, wherein the ratio of the high temperature polymerization inhibitor to the viscosity reducer is about 1:4.

20. The method of claim 1, wherein the first amount is less than the second amount.

\* \* \* \* \*